US008676535B2

(12) United States Patent
Miyamoto

(10) Patent No.: US 8,676,535 B2
(45) Date of Patent: Mar. 18, 2014

(54) ANALYZER

(75) Inventor: Kimiyo Miyamoto, Kakogawa (JP)

(73) Assignee: Sysmex Corporation, Hyogo (JP)

( * ) Notice: Subject to any disclaimer, the term of this patent is extended or adjusted under 35 U.S.C. 154(b) by 1076 days.

(21) Appl. No.: 11/166,209

(22) Filed: Jun. 27, 2005

(65) Prior Publication Data

US 2006/0004541 A1    Jan. 5, 2006

(30) Foreign Application Priority Data

Jun. 30, 2004  (JP) ................................ 2004-193428

(51) Int. Cl.
*G01N 21/05* (2006.01)
*G01N 35/08* (2006.01)

(52) U.S. Cl.
USPC ............. 702/179; 702/180; 702/181; 702/19; 702/22; 702/30; 702/21; 422/73; 422/82.05; 422/68.1

(58) Field of Classification Search
USPC .................................................. 702/179–181
See application file for complete search history.

(56) References Cited

U.S. PATENT DOCUMENTS

| | | | |
|---|---|---|---|
| 4,325,706 A | | 4/1982 | Gershman et al. |
| 5,837,547 A | * | 11/1998 | Schwartz ........................ 436/10 |
| 6,391,263 B1 | | 5/2002 | Mishima et al. |
| 6,525,807 B1 | | 2/2003 | Morikawa et al. |
| 7,267,798 B2 | * | 9/2007 | Chandler .................... 422/82.05 |
| 2003/0030783 A1 | | 2/2003 | Roche et al. |
| 2003/0182072 A1 | * | 9/2003 | Satoh et al. ..................... 702/95 |
| 2004/0018629 A1 | * | 1/2004 | Kawate ........................... 436/63 |

FOREIGN PATENT DOCUMENTS

| | | | |
|---|---|---|---|
| JP | 5-60752 A | | 3/1993 |
| JP | 10-318904 | * | 12/1998 |
| JP | 10-318904 A | | 12/1998 |
| JP | 2004-506876 | | 3/2004 |

OTHER PUBLICATIONS

Akishi et. al. Foreign Translation of JP 05-060752. 16 pages. Dec. 3, 1993.*
Ultrascan. Monte Carlo Histogram. Web Archive <http://web.archive.org/web/20040104065041/http://www.ultrascan.uthscsa.edu/manual/monte_carlo10.png> (Jan. 4, 2004).*

* cited by examiner

*Primary Examiner* — P. Kathryn Wright
(74) *Attorney, Agent, or Firm* — Sughrue Mion, PLLC

(57) ABSTRACT

An analyzer which acquires first measured data relating to a first parameter and second measured data relating to a second parameter, the first and second measured data being obtained by measuring an analyte, forms a two-dimensional distribution chart that indicates a distribution of tangible components contained in the analyte based upon the first and second measured data, with the first and second parameters being set as two axes of the two-dimensional distribution chart, sets an area on the two-dimensional distribution chart, and forms a frequency distribution chart with respect to tangible components belonging to the area, with the first parameter being set as an axis of the frequency distribution chart is disclosed.

11 Claims, 14 Drawing Sheets

ANALYZER

FIELD OF THE INVENTION

The present invention relates to an analyzer, and more specifically concerns an analyzer which outputs a distribution chart on which areas can be set.

BACKGROUND

Conventionally, cytoanalyzers, which allow the operator to set fraction areas on a two-dimensional distribution chart by using a keyboard, have been known. For example, a cytoanalyzer disclosed in Japanese Patent Application Laid-Open No. 5-60752 is listed as the cytoanalyzer of this type. In the cytoanalyzer of this type, the operator is allowed to manually set a fraction area used for discriminating specific cells such as lymphatic corpuscles from the other cells on a two-dimensional distribution chart that indicates the intensities of forward and sideward scattered light rays, and with respect to cells included in the fraction area thus set, an analyzing process for fluorescent characteristics is carried out.

Therefore, in the cytoanalyzer, in order to accurately analyze the fluorescent characteristics of specific cells such as lymphatic corpuscles, accurately setting the fraction area is prerequisite for the analyzing process. Here, in order to accurately set the fraction area, it is necessary for the operator to distinguish an area in which specific cells such as lymphatic corpuscles are present from areas in which the other cells are present.

In the above-mentioned two-dimensional distribution chart, scattered light intensities possessed by respective cells are determined, and with respect to each of the cells, a dot indicating the cell is put on a position corresponding to the scattered light intensity possessed by the cell on a plane so that the chart is formed. Thus, the two-dimensional distribution chart is allowed to indicate the presence or absence of a cell that has a predetermined scattered light intensity. In this arrangement, however, when a plurality of cells have the same scattered light intensity, these cells are represented by a single dot. In other words, the two-dimensional distribution chart fails to indicate the number of cells that have a predetermined scattered light intensity. Consequently, when the operator is only allowed to view the two-dimensional distribution chart, the operator cannot accurately confirm the distribution state of cells. The above-mentioned cytoanalyzer is designed in such a manner that the operator sets a fraction area based upon only the two-dimensional distribution chart of this type; therefore, the operator tends to fail to accurately confirm the distribution state of the cells and consequently fail to set an accurate fraction area.

As described above, in the above-mentioned cytoanalyzer, the operator manually sets a fraction area on a two-dimensional distribution chart. As described in the above-mentioned Japanese Patent Application Laid-Open No. 5-60752, when a plurality of groups of dots indicating cells (groups b, c and d in FIG. 5(a) of the above-mentioned gazette) are placed in a separate manner on the two-dimensional distribution chart, the operator is allowed to set a fraction area; however, when a plurality of groups thereof are placed close to one another, the operator cannot discriminate the respective groups. Consequently, in this case also, the operator cannot set an accurate fraction area.

SUMMARY

The scope of the present invention is defined solely by the appended claims, and is not affected to any degree by the statements within this summary.

The objective of the present invention is to provide an analyzer that allows the operator to accurately set an area.

A first aspect of the present invention is an analyzer that comprises measured data acquiring means for acquiring first measured data relating to a first parameter and second measured data relating to a second parameter, the first and second measured data being obtained by measuring an analyte; two-dimensional distribution chart forming means for forming a two-dimensional distribution chart that indicates a distribution of tangible components contained in the analyte based upon the first and second measured data, with the first and second parameters being set as two axes of the two-dimensional distribution chart; area setting means for setting an area on the two-dimensional distribution chart; and frequency distribution chart forming means for forming a frequency distribution chart with respect to tangible components belonging to the area that is set by the area setting means, with the first parameter being set as an axis of the frequency distribution chart.

A second aspect of the present invention is an analyzer that comprises measured data acquiring means for acquiring first measured data relating to a first parameter and second measured data relating to a second parameter, the first and second measured data being obtained by measuring an analyte; classifying means for classifying tangible components contained in the analyte based upon the first and second measured data; two-dimensional distribution chart forming means for forming a two-dimensional distribution chart that indicates a distribution of the tangible components, with the first and second parameters being set as two axes of the two-dimensional distribution chart; output means for outputting the two-dimensional distribution chart in a manner so as to allow the user to recognize the classification of the tangible components by means of colors; and area setting means for manually setting a manual area on the two-dimensional distribution chart outputted by the output means.

A third aspect of the present invention is an analyzer that comprises distribution chart displaying means for displaying a distribution chart that indicates a distribution of tangible components contained in an analyte; pointer display means for displaying a pointer on the distribution chart; pointer position altering means for altering the position of the pointer on the distribution chart; area setting means for setting an area on the distribution chart based upon the position of the pointer on the distribution chart; and extracting means for extracting tangible components belonging to the area.

DETAILED DESCRIPTION OF THE PREFERRED EMBODIMENTS

The preferred embodiments of the present invention are described hereinafter with reference to the drawings.

A sample analyzer in accordance with one embodiment of the present invention is a cytometer that analyzes blood to count the numbers of white blood corpuscles (WBC), red blood corpuscles (RBC) and platelets (PLT). This sample analyzer is preferably used for blood-analyzing processes for animals. Upon carrying out blood-analyzing processes for animals, an automatic analysis based upon an analyzing algorism, which is normally used, sometimes fails to properly classify blood corpuscles (tangible components). In this case, by carrying out manual analyzing processes as shown below, an appropriate fraction area is set so that the analyzing processes are carried out based upon the fraction area; thus, it becomes possible to carry out blood-analyzing processes for animals with high precision. Moreover, upon carrying out an animal experiment so as to confirm effects of a medicine, there have been demands for setting various fraction areas and for confirming an increase/decrease in number of specific blood corpuscles included in each of the fraction areas, and this sample analyzer can properly satisfies such demands.

1. Total Structure

Figure 1:
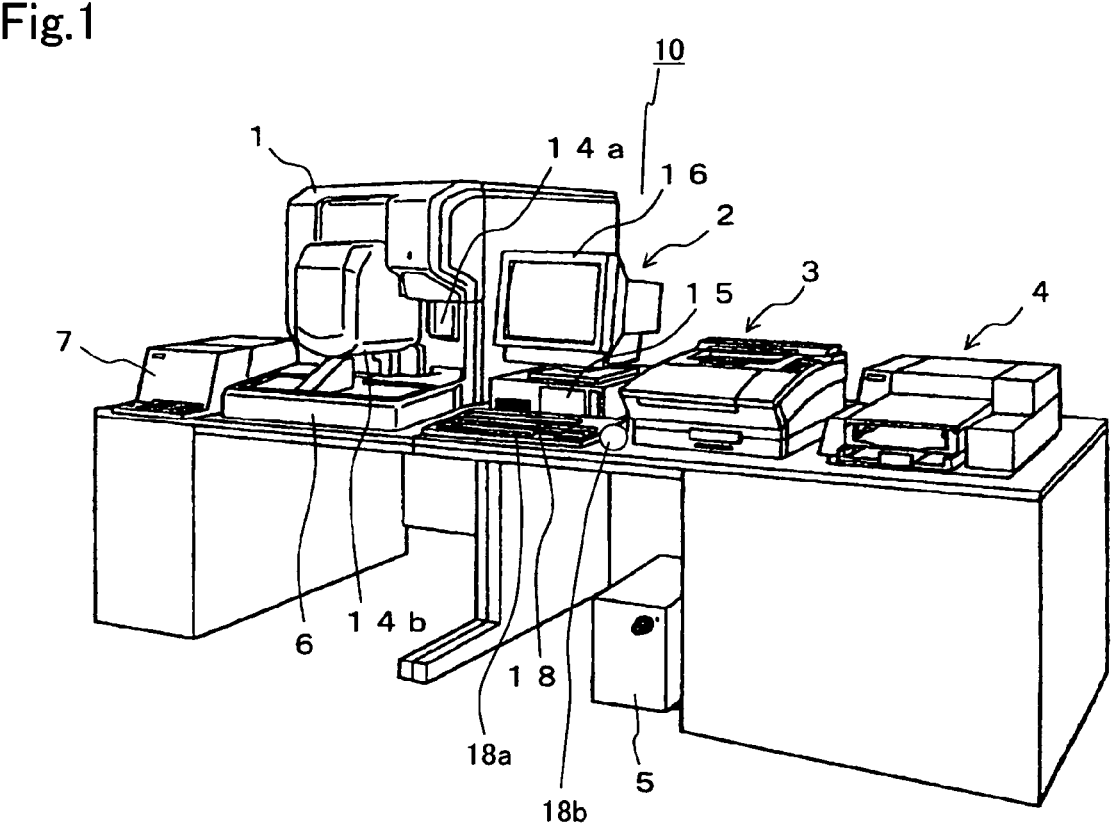
FIG. 1 is a perspective view that shows an entire structure including a sample analyzer and peripheral apparatuses in accordance with one embodiment of the present invention.

As shown in FIG. 1, a sample analyzer 10 of the present embodiment is provided with an apparatus main body 1, and a data processing terminal 2 that is connected to the apparatus main body 1 through a communication cable.

The apparatus main body 1 is connected to an air pressure source 5 that supplies a positive pressure and a negative pressure to the apparatus main body 1 through a tube (not shown). Here, a conveyor 6, which is used for automatically supplying a specimen container containing a specimen to the apparatus main body 1, is connected to the apparatus main body 1. The apparatus main body 1 is connected to a reagent container, not shown, through a tube so that a reagent is absorbed from the reagent container by using negative pressure applied from the air pressure source 5.

The apparatus main body 1 is provided with sample suction units 14a and 14b that carry out a suction process of blood.

The sample suction unit 14a is a suction unit to be used in a manual mode in which the user allows blood to be sucked while he or she is holding a specimen container, and the sample suction unit 14b is a suction unit to be used in a sampler mode in which blood is sucked automatically by using the conveyor 6.

The data processing terminal 2 includes a terminal main body 15, a terminal-side display 16 including a CRT display and a terminal-side input unit 18 including a key board 18a and a mouse 18b.

The data processing terminal 2 is connected to a page printer 3 used for printing a list of analysis results, a color graphic printer 4 used for printing a grain-size distribution chart and a scatter diagram, and a data printer 7 used for printing the analysis results on paper in a test slip format, through respective communication cables.

2. Inner Structure

Figure 2:
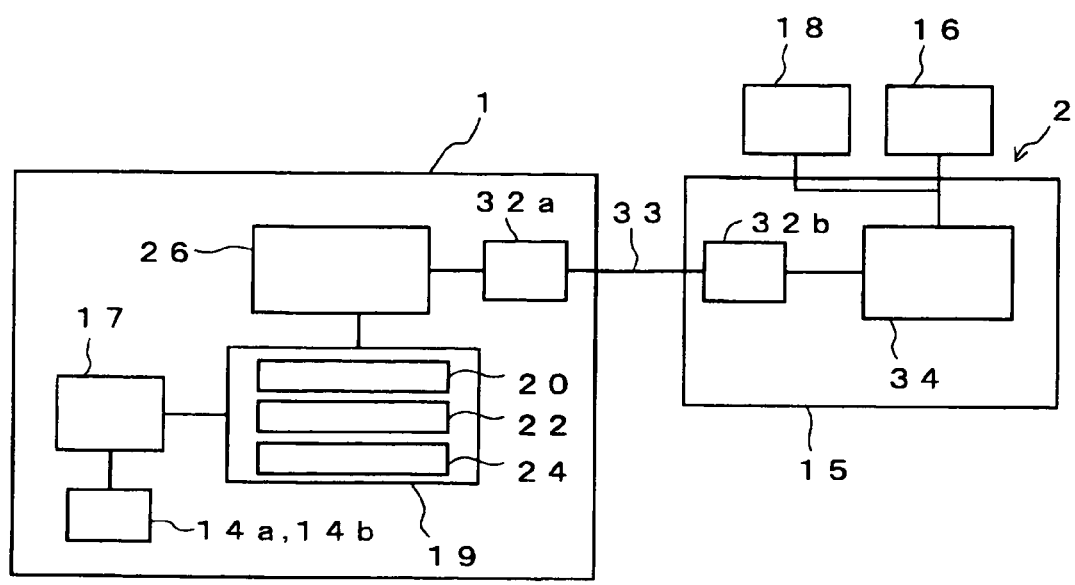
FIG. 2 is a block diagram that shows an inner structure of the sample analyzer shown in FIG. 1.

FIG. 2 is a block diagram that shows inner structures of the apparatus main body 1 and the data processing terminal 2.

As shown in FIG. 2, the apparatus main body 1 includes the sample suction units 14a and 14b, a sample preparation unit 17, a detection unit 19, a main-body-side controller 26 and an input/output interface 32a.

The sample preparation unit 17 carries out processes, such as diluting, blood-dissolving and dyeing processes, by mixing blood sucked by the sample suction units 14a and 14b with a reagent that is sucked from a reagent container, not shown. Thus, a measuring sample, formed through these processes, is supplied to the detection unit 19.

The detection unit 19 includes an optical detection unit 20, electric detection unit 22 and a light-absorption detection unit 24.

The optical detection unit 20 will be described later.

The electric detection unit 22 includes a detector that uses an RF/DC detection method and a detector that uses a sheath flow DC detection method. Here, with respect to the detector that uses the sheath flow DC detection method, for example, a detector disclosed in the specification of U.S. Pat. No. 6,525,807 as the first measuring unit may be used. The detector of this type outputs an electric signal corresponding to the size and inner information of blood corpuscles.

With respect to the light-absorption detection unit 24, a detector, which includes a light-emitting diode, a light-receiving element and a transparent cell placed between these, is used. The light-absorption detection unit 24 outputs an electric signal corresponding to the intensity of light transmitted through only the diluent and an electric signal corresponding to the intensity of light transmitted through a hemoglobin measuring sample to the main-body-side controller 26. The main-body-side controller 26 converts these electric signals to digital signals, and sends the resulting signals to the terminal-side controller 34. The terminal-side controller 34 calculates a difference (light absorption factor) in the transmitted light intensities from these measured data, and then calculates a hemoglobin (HGB) density based upon the light absorption factor.

The main-body-side controller 26, which includes a CPU, ROM, RAM, and A/D converter circuit, converts an electric signal (analog signal) outputted from the detection unit 19 to a digital signal, and transmits the resulting measured data to the data processing terminal 2 through an input/output interface 32a. Moreover, the main-body-side controller 26 controls operations of the sample suction units 14a and 14b, the sample preparation unit 17 and the detection unit 19.

The terminal main body 15 includes an input/output interface 32b and a terminal-side controller 34. The input/output interfaces 32a and 32b are connected to each other through a communication cable 33.

The terminal-side controller 34 includes a CPU, ROM, RAM, hard disk, etc. The terminal-side controller 34 calculates analysis results from measured data transmitted from the apparatus main body 1 through the input/output interface 32b, and allows the terminal-side display 16 to display the results, or allows each of various printers (see FIG. 1) to print the results.

Here, the terminal-side controller 34 is capable of transmitting information inputted from the terminal-side input unit 18 to the apparatus main body 1.

The terminal-side display 16 is provided with a measuring start button used for giving an instruction for the start of measurements to the apparatus main body 1 and a manual analysis start button used for starting a manual analysis, which will be described later, displayed thereon. The user is allowed to select these buttons by using the keyboard 18a and the mouse 18b to instruct the start of measurements and the start of manual analyzing processes. Upon instruction of the manual analyzing processes, the user specifies a scatter diagram to be manually analyzed.

Figure 3:
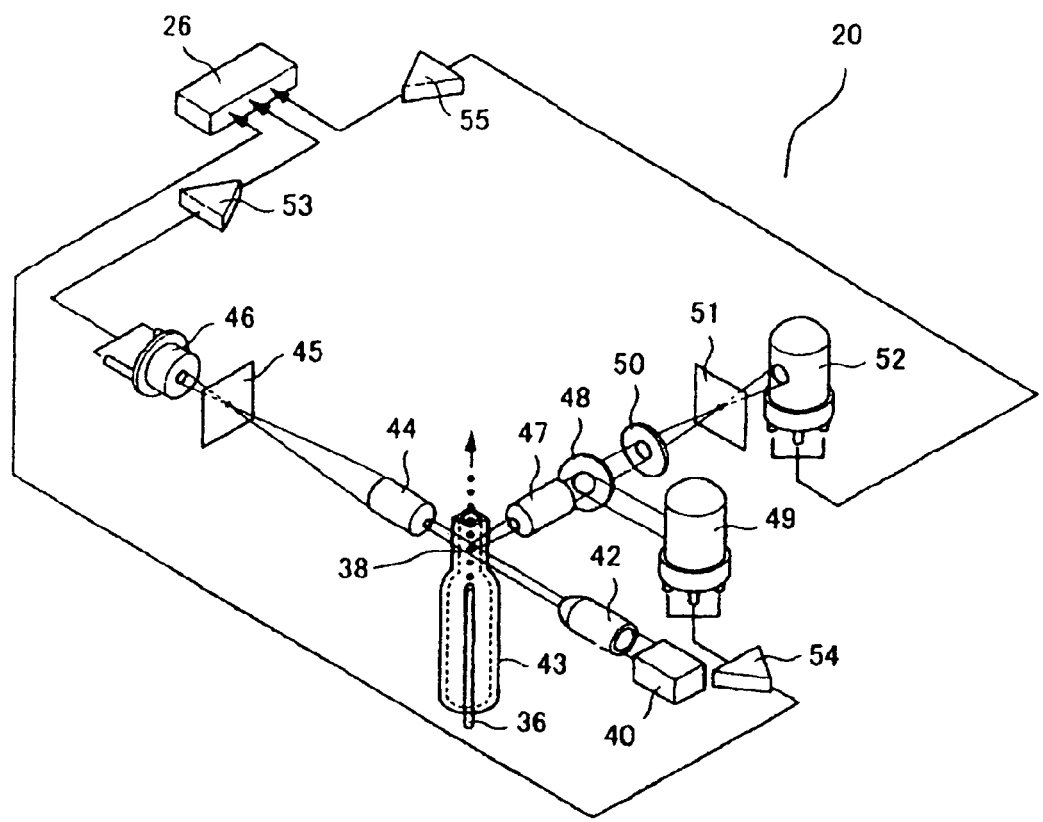
FIG. 3 is a block diagram that shows a structure of an optical detection unit 20 shown in FIG. 2.

FIG. 3 is a perspective view that shows a structure of an optical detection unit 20.

As shown in FIG. 3, the optical detection unit 20 includes a nozzle 36, a laser diode 40, a collimator lens 42, a sheath flow cell 43, a condenser lens 44, a pin-hole plate 45, a photodiode 46, a condenser lens 47, a dichroic mirror 48, a photomultiplier tube 49, a filter 50, a pin-hole plate 51, a photomultiplier tube 52 and amplifiers 53 to 55.

A measuring sample, supplied from the sample preparation unit 17 (see FIG. 2), flows through an orifice unit 38 of the sheath flow cell 43 via the nozzle 36.

Light, emitted from the laser diode 40, is directed to the measuring sample flowing through the orifice unit 38 of the sheath flow cell 43 through the collimator lens 42. Light, which has been scattered forward by the measuring sample flowing through the orifice unit 38 (forward scattered light), is made incident on the photodiode 46 through the condenser lens 44 and the pin-hole plate 45.

Light, which has been scattered sideward by the measuring sample flowing through the orifice unit 38 (sideward scattered light), is made incident on the photomultiplier tube 49 through the condenser lens 47 and the dichroic mirror 48.

Upon irradiation with light, fluorescent light, emitted from the measuring sample flowing through the orifice unit 38 (sideward fluorescent light), is made incident on the photomultiplier tube 52 through the condenser lens 47, the dichroic mirror 48, the filter 50 and the pin-hole plate 51.

The photodiode 46 outputs an electric signal corresponding to the intensity of the forward scattered light (forward scattered light intensity) that has been made incident. The photomultiplier tube 49 outputs an electric signal corresponding to the intensity of the sideward scattered light (sideward scattered light intensity) that has been made incident. The photomultiplier tube 52 outputs an electric signal corresponding to the intensity of the sideward fluorescent light (sideward fluorescent light intensity) that has been made incident.

The electric signal corresponding to the forward scattered light intensity outputted from the photodiode 46, the electric signal corresponding to the sideward scattered light intensity outputted from the photomultiplier tube 49 and the electric signal corresponding to the sideward fluorescent light intensity outputted from the photomultiplier tube 52 are respectively amplified by amplifiers 53, 54 and 55, and inputted to the main-body-side controller 26.

These electric signals are converted to digital signals in the main-body-side controller 26, and the resulting signals are then transmitted to the terminal-side controller 34 in a predetermined data format.

3. Operations of a Sample Analyzer
3-1. Entire Flow

Figure 4:
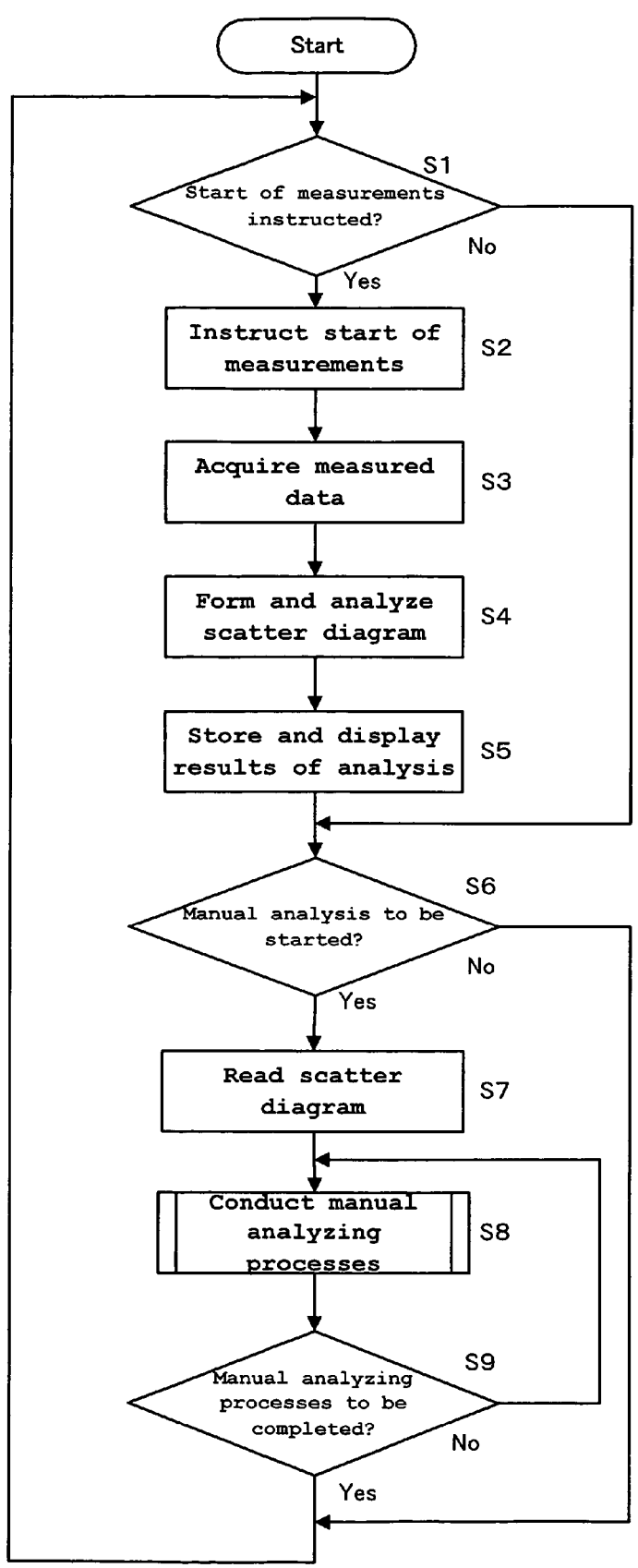
FIG. 4 is a flow chart that explains an outline of processes to be executed by a terminal-side controller 34 shown in FIG. 2.

Referring to FIG. 4, the following description will discuss the outline of processes executed by the terminal-side controller 34.

First, at step S1, the terminal-side controller 34 determines whether or not an instruction for starting measurements has been given by the user, and if the instruction has been given, the sequence proceeds to step S2. If no instruction has been given, the sequence proceeds to step S6.

Next, at step S2, the terminal-side controller 34 gives an instruction to the main-body-side controller 26 to start measuring operations. Upon receipt of the instruction for starting measurements, the main-body-side controller 26 carries out a suction process of blood by using the sample suction unit 14a or 14b depending on the selected suction mode, forms a predetermined measuring sample by using the sample preparation unit 17 and executes processes for detecting a signal from the measuring sample by using each of the detection sections in the detection unit 19. These processes allow the above-mentioned electric signals to enter the main-body-side controller 26 from the respective detection sections of the detection unit 19. The main-body-side controller 26 converts these inputted electric signals to digital signals, and digital-converted measured data are transmitted to the terminal-side controller 34.

Next, at step S3, the terminal-side controller 34 receives the measured data transmitted from the main-body-side controller 26, and stores the data.

At step S4, the terminal-side controller 34 analyzes the measured data received at step S3 to obtain the analysis results of the blood.

More specifically, the terminal-side controller 34 forms a scatter diagram by using the forward scattered light intensity and the sideward fluorescent light intensity as axes of the scatter diagram, based upon pieces of the measured data relating to the sideward scattered light intensity and pieces of the measured data relating to the sideward fluorescent light intensity among the measured data transmitted from the main-body side controller 26, and analyzes white blood corpuscles contained in the blood by analyzing the scatter diagram.

Moreover, the terminal-side controller 34 calculates the number of red blood corpuscles and the number of platelets by using the measured data corresponding to the sizes of red blood corpuscles and platelets as well as to the inner information.

Furthermore, the terminal-side controller 34 calculates a hemoglobin density by using the measured data corresponding to the intensity of transmitted light.

Figure 5:
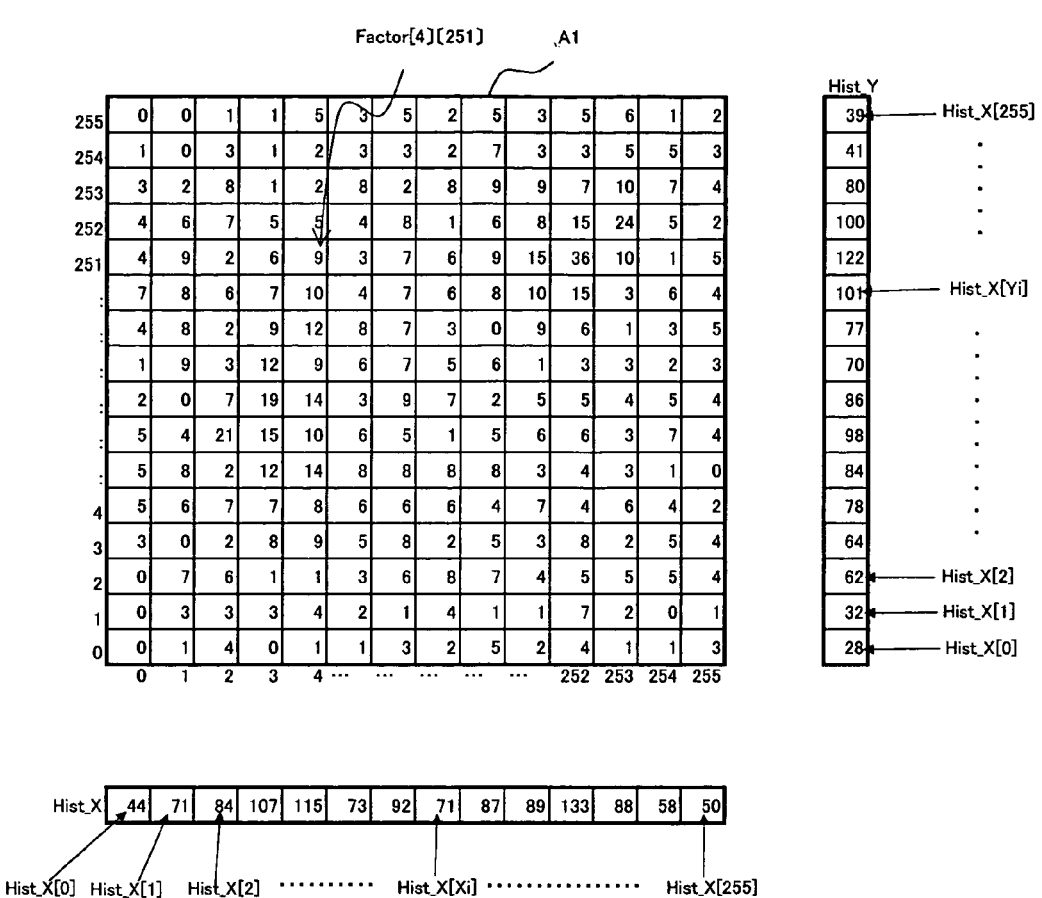
FIG. 5 is an explanatory drawing that shows a structure of a scatter diagram matrix stored in the terminal-side controller 34.

Referring to FIG. 5, the following description will discuss a scatter diagram matrix A1 that uses the sideward scattered light intensity and the sideward fluorescent light intensity as parameters. This scatter diagram matrix A1 is formed by the terminal-side controller 34 at step S4.

The scatter diagram matrix A1 is arranged so that the axis of abscissas indicates the sideward scattered light intensity and the axis of ordinates indicates the sideward fluorescent light intensity; thus, each of the axis of abscissas and the axis of ordinates is divided into 256 sections with respect to each of the sideward scattered light intensity and the sideward fluorescent light intensity. Therefore, the scatter diagram matrix A1 is constituted by 256×256 factors.

Upon forming the scatter diagram matrix A1, the terminal-side controller 34 acquires the sideward scattered light intensity and the sideward fluorescent light intensity for each of blood corpuscles that are flowing through the orifice unit 38 of the sheath flow cell 43, based upon the measured data transmitted from the main-body-side controller 26.

Next, the terminal-side controller 34 places each of blood corpuscles on any one of the factors in the scatter diagram matrix A1 one by one, depending on the sideward scattered light intensity and the sideward fluorescent light intensity.

The terminal-side controller 34 carries out the above-mentioned processes on all the blood corpuscles that have passed through the orifice unit 38 within a predetermined detection time so that the scatter diagram matrix A1 is completed.

Therefore, the numeric value that is given to each of the factors in the scatter diagram matrix A1 represents the number of blood corpuscles that are placed in the respective factors. For example, the number of blood corpuscles, positioned at factor [4][251] (in which the sideward scattered light intensity is in the fifth position from the smallest and the sideward fluorescent light intensity is in the $252^{nd}$ from the smallest), is nine.

With respect to the scatter diagram matrix A1 thus obtained, the terminal-side controller 34 automatically divides the scatter diagram matrix A1 in accordance with a predetermined analyzing algorism so that blood corpuscles belonging to each of fraction areas are calculated.

Next, at step S5, the terminal-side controller 34 stores the above-mentioned analysis results including the scatter diagram matrix A1 and the counted values of the respective blood corpuscles, and also allows the terminal-side display 16 to display the scatter diagram and the counted values. Upon displaying the scatter diagram, the blood corpuscles are displayed in a divided manner with different colors for the respective fraction areas that have been automatically set in accordance with the predetermined analyzing algorism.

At step S6, the terminal-side controller 34 determines whether or not an instruction for starting manual analyzing processes has been given by the user, and if the instruction has been given, the sequence proceeds to step S7. If no instruction has been given, the sequence returns to step S1.

Next, at step S7, the terminal-side controller 34 reads the scatter diagram designated by the user, and allows the terminal-side display 16 to display the scatter diagram.

At step S8, the terminal-side controller 34 carries out manual analyzing processes based upon the fraction areas set by the user. This process will be described later in detail.

Next, at step S9, the terminal-side controller 34 determines whether or not an instruction for completing the manual analyzing processes has been given by the user, and if the instruction has been given, the sequence returns to step S1. If no instruction has been given, the sequence returns to step S8 so as to continue the manual analyzing processes.

3-2 Manual Analysis
3-2-1 Manual Analysis Screen

Figure 6:
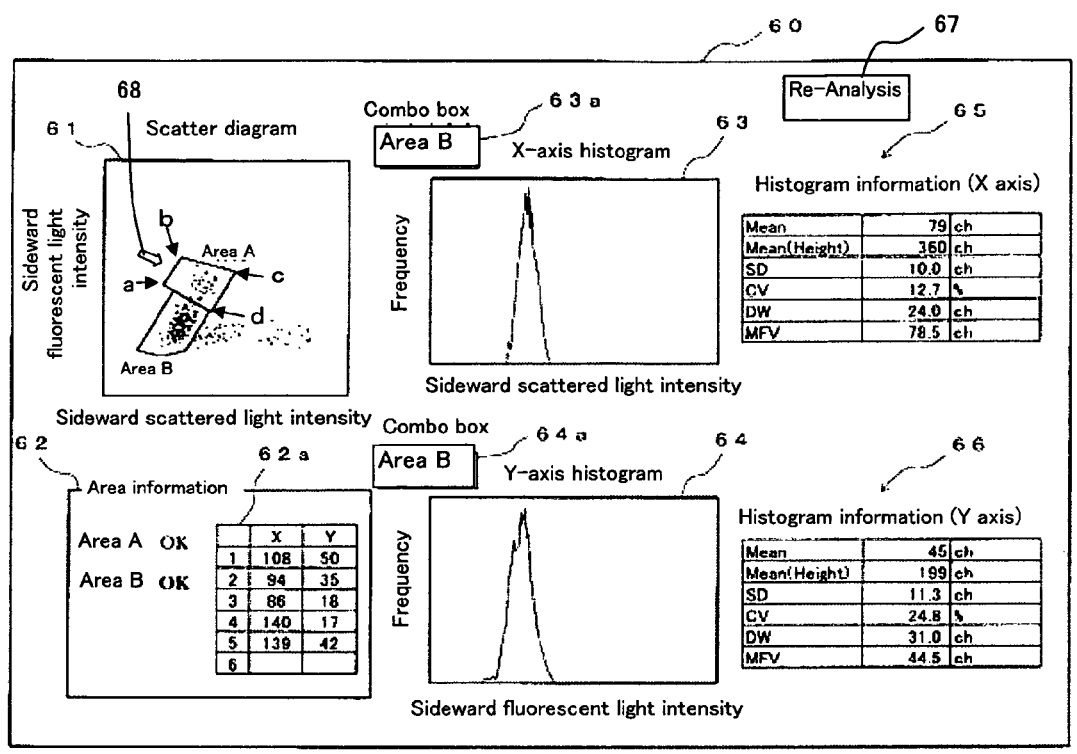
FIG. 6 is a drawing that shows a screen displayed on a main-body-side display 16 shown in FIG. 1 in a manual-analyzing mode.

FIG. 6 shows a screen 60 that is one example of a screen displayed on the terminal-side display 16 during the processes at step S8.

A scatter diagram 61 and area information 62 are placed on the left side of this screen 60. Fraction areas (areas A and B) that have been manually set are shown in the scatter diagram 61. Blood corpuscles (dots), indicated by the scatter diagram 61, are divided into different colors depending on the respective fraction areas (not shown in the screen 60) that have been automatically set by using the analyzing algorism at step S4. Here, regardless of the set positions in areas A and B, these color distinctions are not changed. Therefore, in some cases, blood corpuscles contained in a single area may be indicated by a plurality of colors. Even in such cases, each of histograms, which will be described later, is indicated by a single color. With this arrangement, the user, who carries out manual analyzing processes, is allowed to determine areas without being bothered by the colors that have been automatically set. Alternatively, by reflecting the color distinction information to the histogram, the histogram may be drawn with a plurality of colors.

The following description will discuss setting of areas A and B. Each of these areas has a polygonal shape, and is formed when the user specifies apexes of the polygonal shape by using the mouse 18b.

For example, in the case when an area A is newly set, the user adjusts a mouse pointer 68 at a position a indicated by the scatter diagram 61, and clicks the mouse 18b. Thus, the first apex of area A is determined at the position a. At this time, the terminal-side controller 34 stores coordinate information of the position a. Next, the user drags the mouse pointer 68 to a position b, and clicks the mouse 18b. Thus, the second apex of area A is determined at the position b. At this time, the terminal-side controller 34 stores coordinate information of the position b. Next, the user drags the mouse pointer 68 to a position c, and clicks the mouse 18b. Thus, the third apex of area A is determined at the position c. At this time, the terminal-side controller 34 stores coordinate information of the position c. Next, the user drags the mouse pointer 68 to a position d, and clicks the mouse 18b. Thus, the fourth apex of area A is determined at the position d. At this time, the terminal-side controller 34 stores coordinate information of the position d. Next, the user drags the mouse pointer 68 to the position a, and clicks the mouse 18b. Consequently, a square area A is determined.

Here, in an attempt to form a triangle area, the mouse pointer 68 can be dragged directly from the position c to the position a. Moreover, in an attempt to form a polygonal shape of a pentagon or more, the mouse pointer 68 can be dragged from the position d to still another position, and by clicking the mouse 18b at the corresponding position, the number of apexes is increased.

In the case when the shape of area A that has been formed is altered, the user can adjust the mouse pointer 68 to any one of the apexes of area A, and then clicks the mouse 18b. Moreover, after having dragged the mouse pointer 68 to a desired position, the user again clicks the mouse 18b. At this time, the terminal-side controller 34 stores the coordinate information of the clicked position. Thus, the apex of area A is changed so that the shape of area A is altered. With respect to area B, the shape thereof can be altered in the same manner.

Here, in the sample analyzer of the present embodiment, a plurality of fraction areas are not determined in an overlapped manner.

In area information 62, the coordinate information 62a of each of the apexes of area B is indicated. When area A is selected in the area information 62, the coordinate information of each of the apexes of area A is given.

Histograms (frequency distribution) 63 and 64 respectively relating to the sideward scattered light intensity and the sideward fluorescent light intensity are drawn in the center of the screen 60.

With respect to the histogram of the sideward scattered light intensity, the axis of abscissas indicates the sideward scattered light intensity and the axis of ordinates indicates the number of blood corpuscles (frequency) in each of the sideward scattered light intensities.

In the same manner, with respect to the histogram of the sideward fluorescent light intensity, the axis of abscissas indicates the sideward fluorescent light intensity and the axis of ordinates indicates the number of blood corpuscles (frequency) in each of the sideward fluorescent light intensities.

On the upper left side of each of the histograms, a combo box 63a (64a) is placed. This combo box 63a (64a) on this screen 60 allows selection of any one of the total area, area A, area B and the entire area. When "the total area" is selected, histograms are drawn with respect to all the blood corpuscles within the scatter diagram 61. When "area A" or "area B" is selected, a histogram is drawn with respect to the blood corpuscles belonging to the selected area.

"The entire area" represents area A and area B, and when "the entire area" is selected, histograms are drawn with respect to the blood corpuscles belonging to area A and the blood corpuscles belonging to area B.

With respect to the histogram upon selection of the entire area, different kinds of colors or lines may be used between the blood corpuscles belonging to area A and the blood corpuscles belonging to area B. This arrangement allows the user to distinguish the areas on the histogram.

Moreover, even when any one of the areas is selected, histograms with respect to all the areas may always be displayed.

The histograms 63 and 64 represent histograms that are displayed upon selection of area B.

Figure 15:
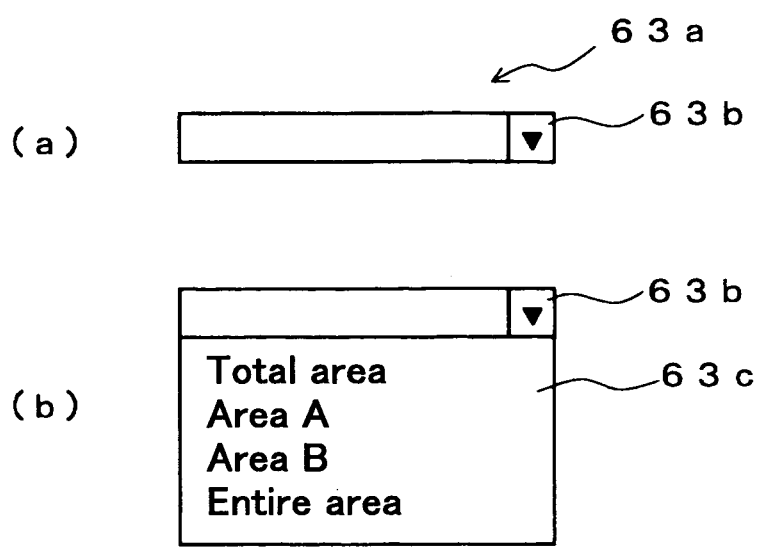
FIG. 15 is a drawing that explains functions of a combo box displayed on the screen shown in FIG. 6.

As shown in FIG. 15(a), the combo box 63a is provided with an arrow portion 63b, and when the arrow portion 63b is clicked by using the mouse 18b, a list box 63c is displayed, as shown in FIG. 15(b).

This list box 63c is designed so that areas, which correspond to areas that have been set in the scatter diagram 61 (area A and area B in the example of FIG. 6), "the total area", and "the entire area" are displayed.

In the case when the user selects any one of the areas from the list box 63c by using the mouse 18b, a drawing ID corresponding to the selected area is temporarily stored in the terminal-side controller 34. The drawing ID is an ID used for specifying the selected area, and a drawing ID "1" is assigned to "the total area", a drawing ID "2" is assigned to "area A", a drawing ID "3" is assigned to "area B" and a drawing ID "4" is assigned to "the entire area", respectively.

On the right side of the screen 60, pieces of histogram information 65 and 66 corresponding to the sideward scattered light intensity and the sideward fluorescent light intensity are displayed. The pieces of histogram information 65 and 66, which represent statistical data relating to the histograms 63 and 64, include an average value, dispersion and a half-value width.

On the upper right side of the screen 60, a re-analyzing button 67 is displayed. When the user shifts the mouse pointer 68 through the mouse 18b to select the re-analyzing button 67, blood corpuscles, contained in the areas set in the scatter diagram 61, are counted for each of the areas.

The user of the apparatus of the present embodiment is allowed to confirm whether or not fraction areas manually set are appropriate, by viewing the shapes of the scatter diagram 61, the histograms 63 and 64 as well as the pieces of histogram information 65 and 66. For example, when the shapes of the histograms 63 and 64 form normal distributions, it is highly possible that the corresponding fraction area is appropriate. For example, when the skirt portion of the peak in the histogram 63 or 64 has broken off unnaturally, it is highly possible that the corresponding fraction area is inappropriate. When it has been determined that the fraction area is appropriate, the setting process of the fraction area is completed. When it has been determined that the fraction area is inappropriate, a resetting process of the fraction area is carried out. After the resetting process, histograms for the fraction area that has been reset are drawn. Here, as described earlier, the resetting process of the fraction area is carried out through operations in which the user adjusts the mouse pointer 68 to any one of the apexes of area A or area B, and then clicks the mouse 18b and, after the mouse pointer 68 has been dragged to a desired position, the mouse 18b is again clicked.

3-2-2. Histogram Drawing Process

The following description will discuss processes at step S8. In these processes, a process for setting a fraction area in the scatter diagram 61 (steps S11 and S12), a process for setting combo boxes 63a and 64a (steps S14 to S16) and a process for conducting a re-analysis (steps S101 to S103) are executed in parallel with one another.

Figure 7:
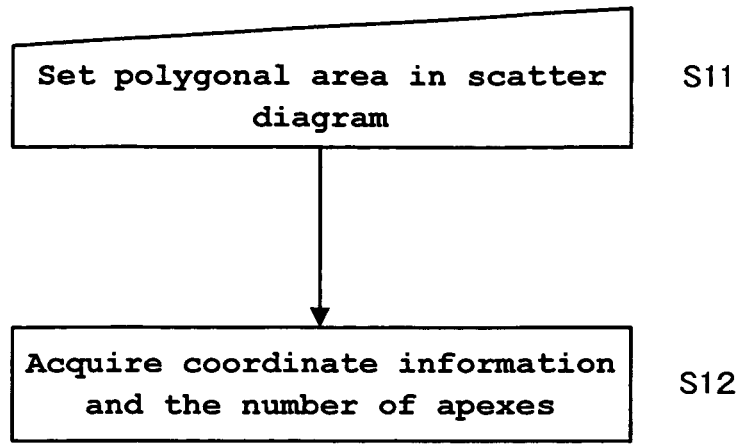
FIGS. 7 and 8 are flow charts that explain processes in step S8 shown in FIG. 4, in detail.

As shown in FIG. 7, when a polygonal area is set within the scatter diagram 61 by the user through the aforementioned method (step S11), the terminal-side controller 34 acquires coordinate information of each of the apexes and the number of the apexes of the polygon (area A and area B in the example of FIG. 6) (step S12).

Figure 8:
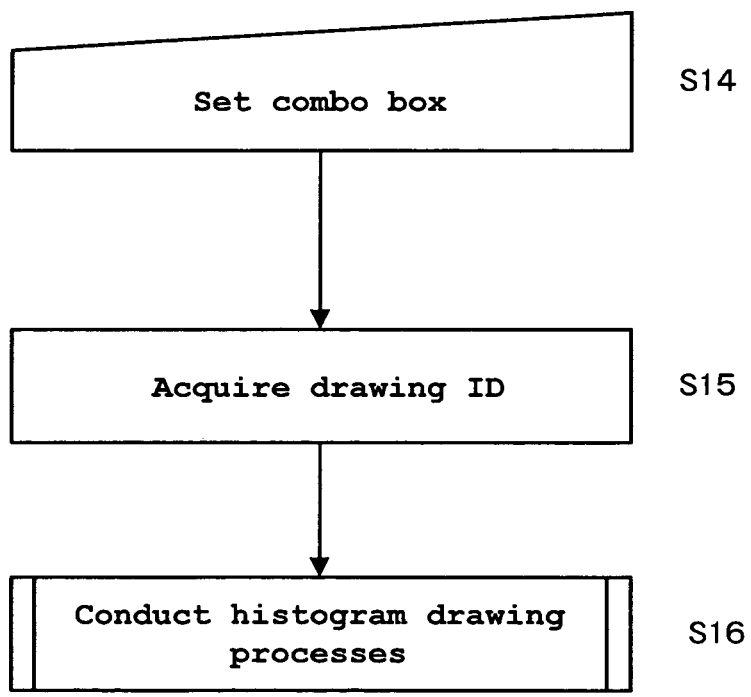

When the polygonal area has been set in the scatter diagram 61, a setup of each of combo boxes 63a and 63b is accepted (step S14), as shown in FIG. 8. In this step, the user is allowed to select any one of the areas from a list box 63c by using the mouse 18b.

When the user selects anyone of the areas, the terminal-side controller 34 temporarily stores a drawing ID corresponding to the selected area (step S15).

Moreover, the terminal-side controller 34 executes a drawing process of a histogram corresponding to the selected area (step S16).

Referring to FIG. 5 and FIGS. 9 to 13, the following description will discuss a histogram drawing process (step S16). For convenience of explanation, for example, the histogram 63 of the sideward scattered light intensity is explained; however, the same processes are also carried out on the histogram 64 of the sideward fluorescent light intensity. Moreover, even in the case when the shape of the polygonal area within the scatter diagram 61 is altered, the histograms of the sideward scattered light intensity and the sideward fluorescent light intensity are drawn by using the same processes as those of step S16, with respect to the area selected by using the combo box.

In the processes of step S16 described below, a histogram matrix (Hist_X and Hist_Y) shown in FIG. 5 is used. Hist_X is constituted by 256 factors. Numeric values are inputted to the respective factors. The numeric values of the respective factors are indicated by Hist_X[0], Hist_X[1], Hist_X[2] ... Hist_X[Xi] ... Hist_X[255] in succession from the left side in FIG. 5.

In the same manner, Hist_Y is constituted by 256 factors. Numeric values are inputted to the respective factors. The numeric values of the respective factors are indicated by Hist_Y[0], Hist_Y[1], Hist_Y[2] ... Hist_Y[Yi] ... Hist_Y[255] in succession from below in FIG. 5.

Figure 9:
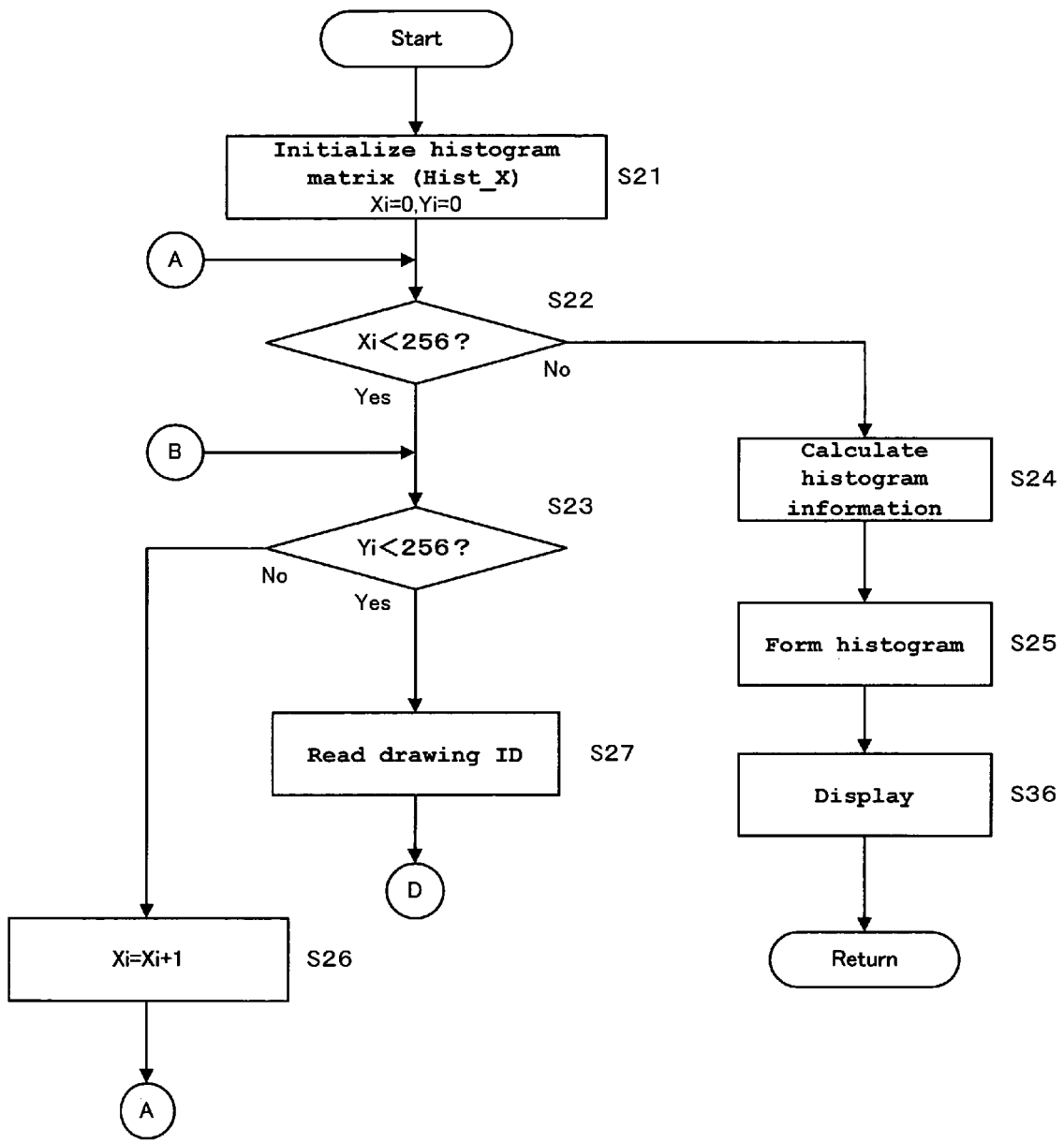
FIGS. 9 to 13 are flow charts that explain processes in step S16 shown in FIG. 8, in detail.

First, at step S21 of FIG. 9, the terminal-side controller 34 initializes the histogram matrix (Hist_X). More specifically, all the numeric values contained in the respective factors of Hist_X are set to 0. Moreover, the terminal-side controller 34 sets values of Xi and Yi to 0.

Next, at step S22, the terminal-side controller 34 confirms the value of Xi, and when the value of Xi is smaller than 256, the sequence proceeds to a process of step S23. When the value of Xi has reached 256, the sequence proceeds to a process of step S24.

At step S23, the value of Yi is confirmed, and when the value of Yi is smaller than 256, the sequence proceeds to a process of step S27. When the value of Yi has reached 256, the sequence proceeds to a process of step S26.

At step S27, the terminal-side controller 34 reads the drawing ID that has been temporarily stored at step S15. Then, the sequence proceeds to step S31 of FIG. 10.

Figure 10:
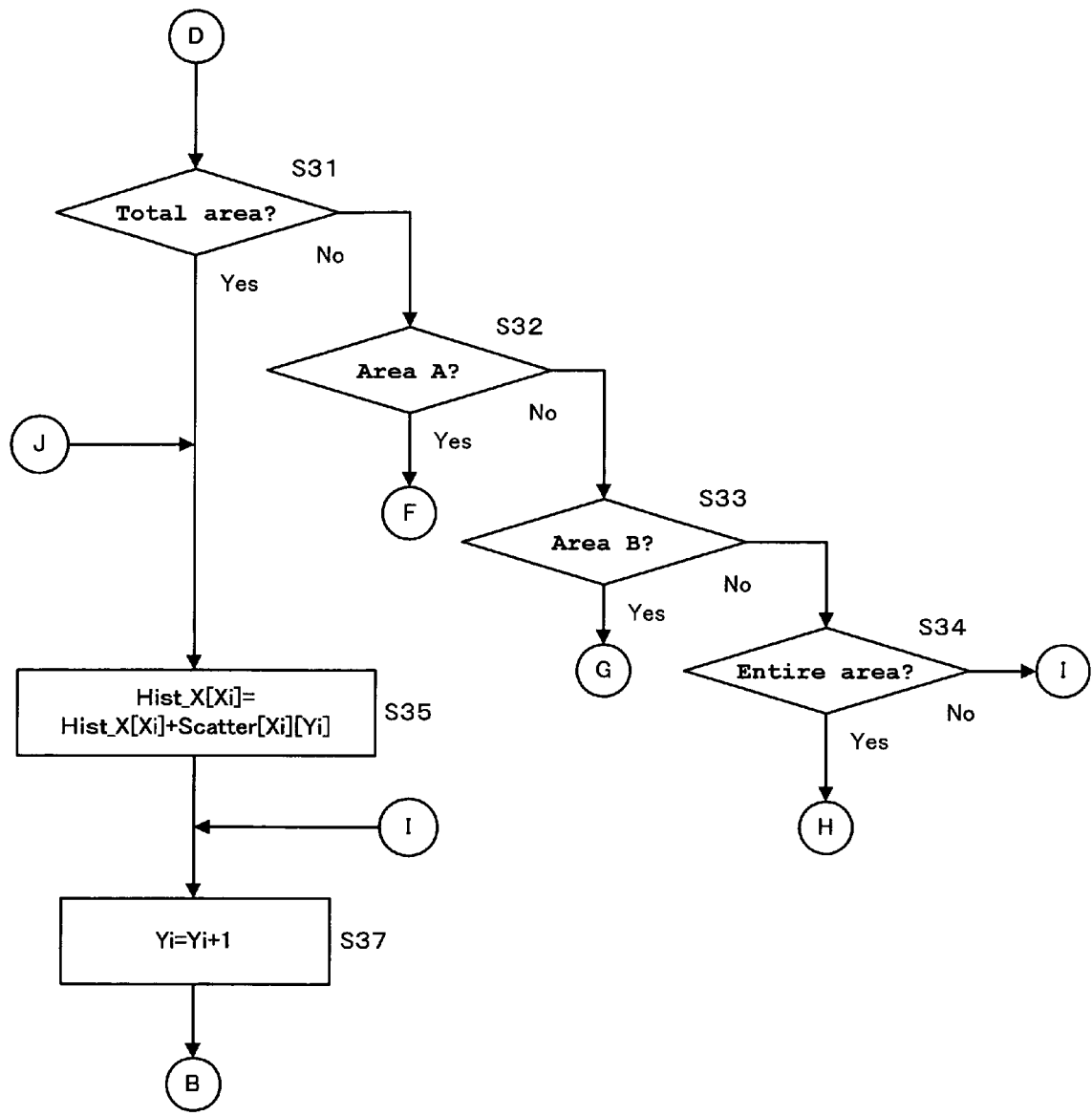
Figure 11:
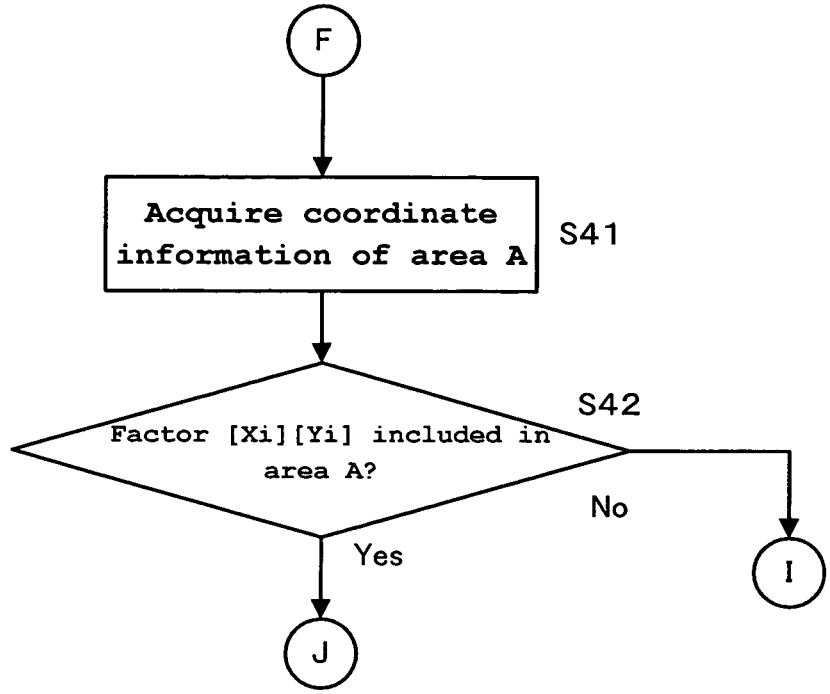
Figure 12:
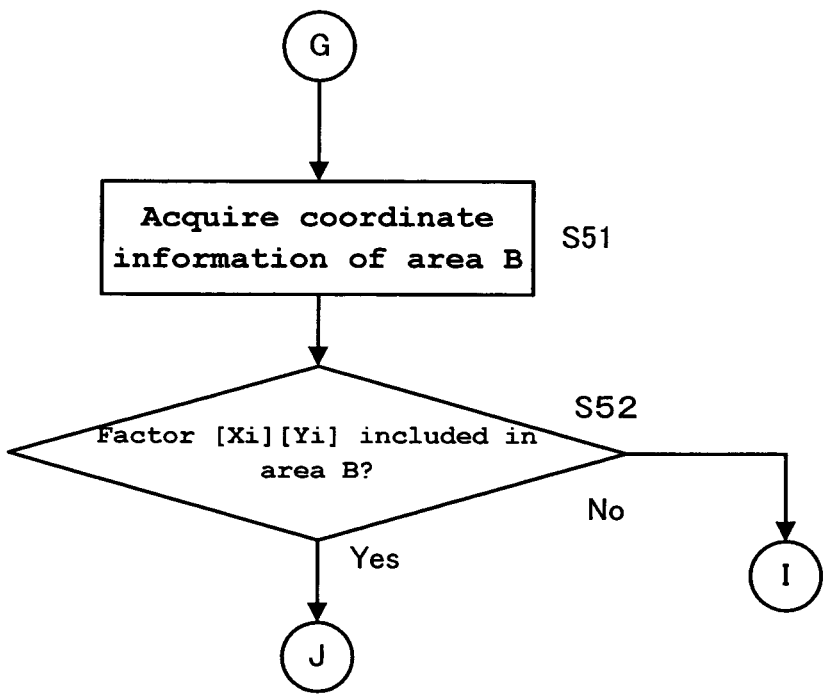
Figure 13:
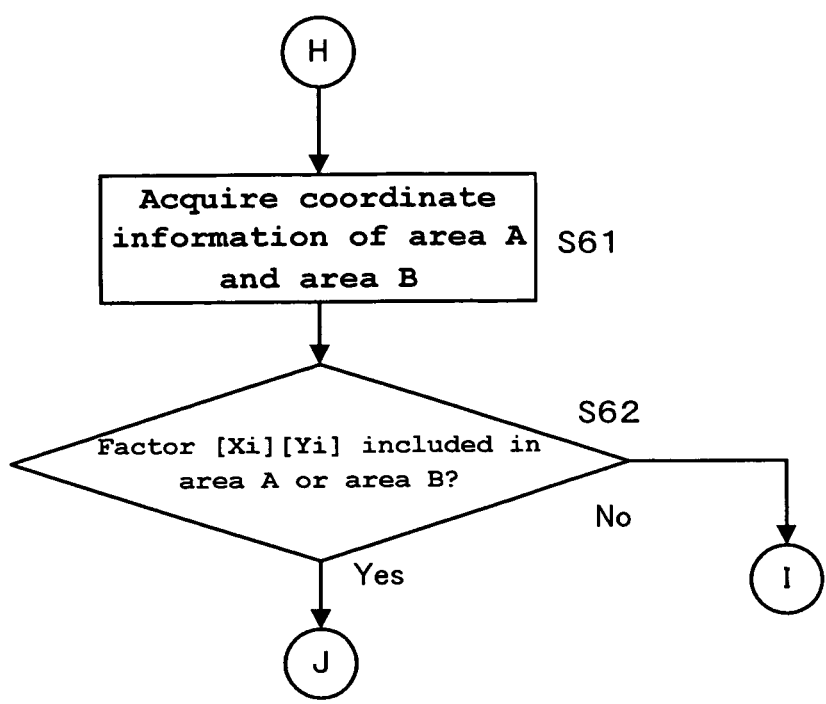

At step S31 of FIG. 10, it is determined whether or not the drawing ID read at step S27 is an ID corresponding to "the total area". When the drawing ID is the ID corresponding to "the total area", the sequence proceeds to processes at step S35; in contrast, when it is not the ID corresponding to "the total area", the sequence proceeds to step S32.

At step S35, the terminal-side controller 34 adds Scatter [Xi] [Yi] to Hist_X[Xi] so that the resulting numeric value is set as new Hist_X[Xi].

Here, Scatter[Xi][Yi] refers to a numeric value that is inputted to factor [Xi] [Yi] (having the Xi-th sideward scattered light intensity from the smallest and the Yi-th sideward fluorescent light intensity from the smallest) in the scatter diagram matrix A1 (FIG. 5).

At step S32, it is determined whether or not the drawing ID read at step S27 is the ID corresponding to "only area A". When the drawing ID is the ID corresponding to "only area A", the sequence proceeds to step S41 (FIG. 11), and when it is not the ID corresponding thereto, the sequence proceeds to step S33.

At step S41, the coordinate information of area A (information about coordinates of apexes of the polygon) stored at step S12 is read out.

At step S42, based upon the coordinate information read at step S41, it is determined whether or not factor [Xi] [Yi] in the scatter diagram matrix is included in area A.

When factor [Xi][Yi] is included in area A, the sequence proceeds to step S35 so that a numeric value obtained by adding Scatter[Xi][Yi] to Hist_X[Xi] is set as new Hist_X [Xi].

When factor [Xi] [Yi] is not included in area A at step S42, the sequence proceeds to step S37.

At step S33, it is determined whether or not the drawing ID read at step S27 is the ID corresponding to "only area B". When the drawing ID is the ID corresponding to "only area B", the sequence proceeds to step S51 (FIG. 12), and when it is not the ID corresponding thereto, the sequence proceeds to step S34.

At step S51, the coordinate information of area B stored at step S12 is read out, and the sequence proceeds to step S52.

At step S52, based upon the coordinate information read at step S51, it is determined whether or not factor [Xi] [Yi] in the scatter diagram matrix is included in area B.

When factor [Xi] [Yi] is included in area B, the sequence proceeds to step S35 so that a numeric value obtained by adding Scatter[Xi] [Yi] to Hist_X[Xi] is set as new Hist_X [Xi].

When factor [Xi] [Yi] is not included in area B at step S52, the sequence proceeds to step S37.

At step S34, it is determined whether or not the drawing ID read at step S27 is the ID corresponding to "the entire area". When the drawing ID is the ID corresponding to "the entire area", the sequence proceeds to step S61 (FIG. 13), and when it is not the ID corresponding thereto, the sequence proceeds to step S37.

At step S61, the coordinate information about area A and area B stored at step S12 is read out, and the sequence proceeds to step S62.

At step S62, based upon the coordinate information read at step S61, it is determined whether or not factor [Xi] [Yi] in the scatter diagram matrix is included in area A or area B.

When factor [Xi] [Yi] is included in area A or area B, the sequence proceeds to step S35 so that a numeric value obtained by adding Scatter[Xi] [Yi] to Hist_X[Xi] is set as new Hist_X[Xi].

When factor [Xi] [Yi] is not included in area B at step S62, the sequence proceeds to step S37.

By using the above-mentioned processes, among numeric values inputted to the respective factors of the scatter diagram matrix, only the numeric values contained in the selected area can be extracted and reflected to the histogram matrix Hist_X.

Here, in the present embodiment, only one histogram matrix is used; however, two histogram matrixes Hist1_X and Hist2_X may be prepared, and at step S35, when factor [Xi] [Yi] is included in area A, Scatter [Xi] [Yi] may be added to Hist1_X[Xi], while, when factor [Xi] [Yi] is included in area B, Scatter [Xi] [Yi] may be added to Hist2_X[Xi]. With this arrangement, upon drawing the histograms, it becomes possible to give different colors to the respective areas.

At step S37, the terminal-side controller 34 sets Yi to Yi+1, and the sequence returns to a process at step S23. This process allows preparation for carrying out the above-mentioned processes on factors having a level higher by one level in the sideward fluorescent light intensity in the scatter diagram.

At step S26, the terminal-side controller 34 sets Xi to Xi+1, and the sequence returns to a process at step S22. This process allows preparation for carrying out the above-mentioned processes on factors having a level higher by one level in the sideward scattered light intensity in the scatter diagram.

At step S24, based upon Hist_X thus completed, the terminal-side controller 34 calculates histogram information 65 (see FIG. 6).

At step S25, based upon Hist_X thus completed, the terminal-side controller 34 forms a histogram 63 (see FIG. 6).

At step S36, the terminal-side controller 34 allows the terminal-side display 16 to display a screen 60 including the histogram 63 and histogram information 65 acquired at step S24 and step S25.

Figure 14:
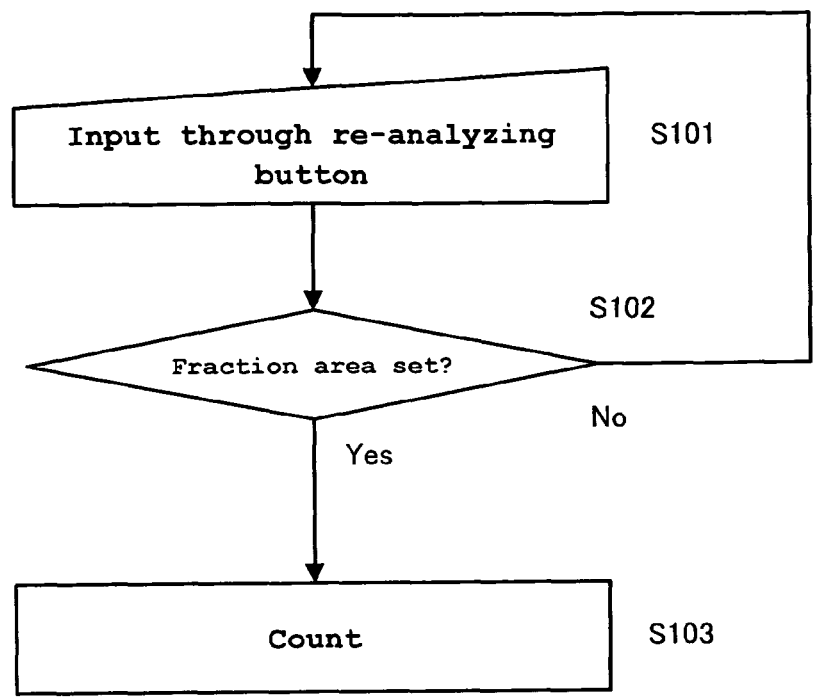
FIG. 14 is a flow chart that explains processes in step S8 shown in FIG. 4 in detail.

As shown in FIG. 14, the terminal-side controller 34 executes a process for accepting an input from a re-analyzing button 67 (step S101). Here, this process is executed in parallel with processes (steps S11 and S12) in which a fraction area is set in the scatter diagram 61 and processes (steps from S14 to S16) in which combo boxes 63a and 64a are set therein.

When an input is given by the user through the re-analyzing button 67 (step S101), the terminal-side controller 34 determines whether or not any fraction areas have been set in the scatter diagram 61 at step S102.

When it is determined that no fraction area has been set at step S102, the sequence returns to the process for accepting an input from the re-analyzing button 67.

At step S102, when it is determined that fraction areas have been set, the terminal-side controller 34 calculates blood corpuscles contained in each of the fraction areas that have been set, at step S103.

Here, the number of blood corpuscles counted at step S103 is displayed on the screen when the user carries out an operation so as to display the re-analysis result screen (not shown).

Embodiment 2

Figure 16:
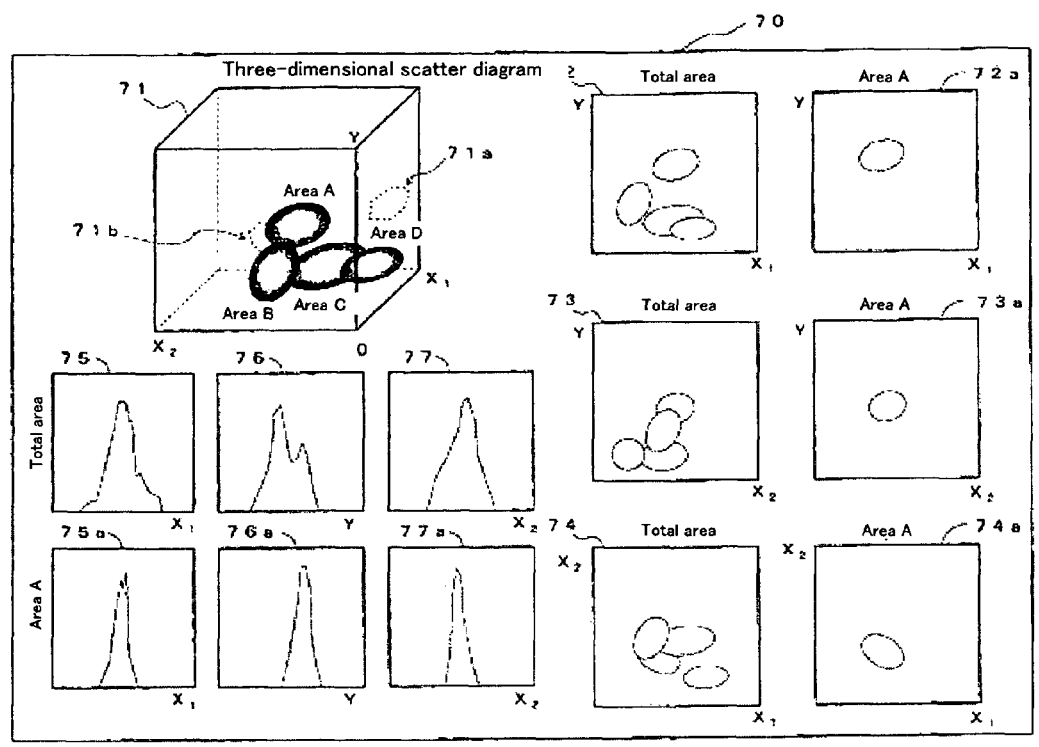
FIG. 16 is a drawing that shows a screen displayed on a display of a sample analyzer in a manual-analyzing mode, in accordance with another embodiment of the present invention.

FIG. 16 shows a screen 70 in a manual analysis mode in a sample analyzer (cytometer) relating to another embodiment. In the aforementioned embodiment, fraction areas are manually set in the scatter diagram 61 indicated as a two-dimensional distribution chart, and with respect to blood corpuscles in each of the fraction areas, histograms 63 and 64 are formed; however, in the present embodiment, fraction areas are set in a three-dimensional distribution chart, and with respect to blood corpuscles in each of the fraction areas, scatter diagrams and histograms are formed.

On the upper left side of the screen 70, a three-dimensional distribution chart 71 is drawn based upon measured data relating to three parameters $X_1$, $X_2$ and Y. $X_1$, $X_2$ and Y respectively represent the forward scattered light intensity, the sideward scattered light intensity and the sideward fluorescent light intensity. In the three-dimensional distribution chart 71, fraction areas, indicated by areas A to D, are set. The shape of these fraction areas is not particularly limited. With respect to the fraction areas, for example, on each of $X_1$-Y plane and $X_2$-Y plane, fraction areas 71a and 71b having a polygonal shape are set by using the same method as that of embodiment 1, and a three-dimensional space, which is formed by an overlapped portion between a three-dimensional space that extends in the $X_2$ direction through the fraction area 71a and a three-dimensional space that extends in the $X_1$ direction through the fraction area 71b, is determined as a fraction area.

Symbols 72 to 74 indicate scatter diagrams that are obtained by projecting all the areas of the three-dimensional scatter diagram onto the $X_1$-Y plane, $X_2$-Y plane and $X_1$-$X_2$ plane. Symbols 72a to 74a indicate scatter diagrams that are obtained by projecting only the selected fraction area (area A) onto the $X_1$-Y plane, $X_2$-Y plane and $X_1$-$X_2$ plane.

As clearly indicated by the scatter diagrams 73, 74 and the like, with respect to the scatter diagram relating to all the areas, it is difficult to identify area A because of a plurality of areas that are overlapped with one another; however, with respect to the scatter diagrams 72a to 74a relating to only area A, it is easy to identify area A. Therefore, the user determines whether or not the distribution of blood corpuscles belonging to area A is appropriate by viewing the scatter diagrams 72a to 74a, and if it is inappropriate, the fraction area in the three-dimensional distribution chart 71 is changed; thus, it becomes possible to easily set an appropriate fraction area.

Moreover, symbols 75 to 77 indicate histograms that are obtained by projecting all the areas of the three-dimensional scatter diagram onto the $X_1$, Y and $X_2$ axes. Symbols 75a to 77a indicate histograms that are obtained by projecting only the selected fraction area (area A) onto the $X_1$, Y and $X_2$.

As clearly indicated by the histograms 75 to 77, with respect to the histogram relating to all the areas, it is difficult to identify area A because of a plurality of areas that are overlapped with one another; however, with respect to the histograms 75a to 77a relating to only area A, it is easy to identify area A. Therefore, the user determines whether or not the distribution of tangible components belonging to area A is appropriate by viewing the histograms 75a to 77a, and if it is inappropriate, the fraction area in the three-dimensional scatter diagram 71 is changed; thus, it becomes possible to easily set an appropriate fraction area.

The explanation has been given by exemplifying a case in which area A is selected; however, in the case when another area is selected, the scatter diagrams and histograms relating to tangible components belonging to the corresponding area are drawn.

With respect to the method for drawing scatter diagrams and histograms relating to only the blood corpuscles belonging to a fraction area, basically, the same method as that of the aforementioned embodiment is used. In the aforementioned embodiment, among numeric values inputted to the respective factors of a scatter diagram, only those numeric values belonging to the selected fraction area are reflected to Hist_X so that the histogram is drawn.

In contrast, in the present embodiment, a three-dimensional scatter diagram matrix having the forward scattered light intensity, the sideward scattered light intensity and the sideward fluorescent light intensity as parameters may be prepared, and among the respective factors in this scatter diagram matrix, only those factors relating to the selected fraction area may be reflected to a two-dimensional scatter diagram matrix and a histogram matrix Hist_X.

Thus, with respect to only the blood corpuscles belonging to the selected fraction area, scatter diagrams and histograms can be drawn.

Here, the histogram matrix Hist_X may be formed based upon the completed two-dimensional scatter diagram matrix, and in this case, the histogram matrix Hist_X can be formed by using the same method as that of step S16 of the aforementioned embodiment.

In the above-mentioned embodiments, the scatter diagram and the frequency distribution chart (histogram) are displayed on the same screen (area setting screen) 60 on a display; however, the present invention is not intended to be limited by this structure, and these may be displayed on respectively different screens. Moreover, the area setting screen may be printed by a printer.

Moreover, in the above-mentioned embodiments, the two-dimensional distribution chart having the sideward fluorescent light intensity and the sideward scattered light intensity as axes or the three-dimensional distribution chart having the forward scattered light intensity, the sideward scattered light intensity and the sideward fluorescent light intensity as axes is used; however, the present invention is not intended to be limited by this structure, and with respect to the axes of the distribution chart, various parameters, such as the forward scattered light intensity and transmitted light intensity, may be used.

In the above-mentioned embodiments, explanations have been given by exemplifying a cytometer; however, the present invention is not intended to be limited by this apparatus, and may be applied to various analyzers, such as a particle analyzer used for analyzing particles such as toner particles and a urine analyzer used for analyzing tangible components in urine.

In the above-mentioned embodiments, explanations have been given by exemplifying a sample analyzer used for measuring an animal blood; however, the present invention is not intended to be limited by this, and may be applied to a sample analyzer used for measuring a human blood, or may be applied to a sample analyzer used for measuring body fluids other than blood, such as an alveolar rinsing liquid.

In the above-mentioned embodiments, blood corpuscles included in a single fraction area are indicated on a histogram by using a single color; however, the present invention is not intended to be limited by this arrangement, and the colors of blood corpuscles (dots) on the histogram may be changed in association with colors displayed on the scatter diagram.

In the above-mentioned embodiments, with respect to the histogram, the frequency is indicated on the axis of ordinates; however, the present invention is not intended to be limited by this arrangement, and the frequency may be indicated on the axis of abscissas, with parameters, such as the sideward scattered light intensity and the sideward fluorescent light intensity, being indicated on the axis of ordinates.

In the above-mentioned embodiments, the number of blood corpuscles contained in a fraction area is counted; however, the present invention is not intended to be limited by this arrangement, and the blood corpuscles contained in the fraction area may be further distributed on a scatter diagram using other parameters so that the blood corpuscles can be classified by using the corresponding scatter diagram.

In addition, the present invention includes a computer program product to be used for operating the terminal-side controller 34 of the above-mentioned embodiments in the above-mentioned manner.

What is claimed is:
1. An analyzer for analyzing blood of non-human animals comprising:
   a measured data acquiring device configured to measure a blood sample collected from a non-human animal and to acquire first measured data relating to a first parameter and second measured data relating to a second param- eter, the first and second measured data being obtained by measuring the blood sample;
an input device;
a display; and
a controller configured:
- to classify blood cells contained in the blood sample into a plurality of groups based upon the first and second measured data;
- to form a two-dimensional distribution chart that indicates a distribution of the blood cells contained in the blood sample based upon the first and second measured data, with the first and second parameters being set as two axes of the two-dimensional distribution chart;
- to control the display to display the two-dimensional distribution chart;
- to draw a plurality of areas on the two-dimensional distribution chart in accordance with data input by a user through the input device;
- to form first and second frequency distribution charts with respect to blood cells belonging to one of the areas drawn by the input device on the two-dimensional distribution chart, with the first parameter being set as an axis of the first frequency distribution chart and the second parameter being set as an axis of the second frequency distribution chart;
- to control the display to display a screen including, alongside one another, the two-dimensional distribution chart on which the areas have been drawn, the first frequency distribution chart, and the second frequency distribution chart;
- to form, in response to an alteration of a shape of the one of the areas, the first and second frequency distribution charts with respect to those blood cells belonging to the one of the areas having the altered shape; and
- to control the display to display the first and second frequency distribution charts formed in response to the alteration of the shape of the one of the areas,
wherein the controller is further configured to receive a selection of the one of the areas in which the first and second frequency distribution charts are formed.

2. The analyzer according to claim 1, wherein the controller is further configured to form third and fourth frequency distribution charts with respect to all of the blood cells belonging to the two-dimensional distribution chart and to control the display to display a screen including the third and fourth frequency distribution charts, with the first parameter being set as an axis of the third frequency distribution chart and the second parameter being set as an axis of the fourth frequency distribution chart.

3. The analyzer according to claim 1, wherein the first and second frequency distribution charts are distribution charts in which the frequency of blood cells belonging to the one of the areas are represented by a single color.

4. The analyzer according to claim 1, wherein the controller is further configured to calculate statistical data based upon the first or second frequency distribution chart.

5. The analyzer according to claim 1, wherein
the controller is further configured to control the display to display a pointer on the two-dimensional distribution chart;
the input device is configured to alter a position of the pointer on the two-dimensional distribution chart; and
the controller is further configured to draw the one of the areas based upon the position of the pointer on the two-dimensional distribution chart.

6. The analyzer according to claim 1, wherein the first parameter is a scattered light intensity or a fluorescent light intensity.

7. The analyzer according to claim 1, wherein the controller controls the display so that colors respectively associated with each group of the plurality of groups differ from group to group on the two-dimensional distribution chart.

8. The analyzer according to claim 7, wherein the controller is further configured to retain the respective colors associated with the blood cells, even when the one of the areas has been altered.

9. The analyzer according to claim 7, wherein the controller is further configured to count blood cells of a predetermined group and blood cells belonging to one of the areas.

10. An analyzer for analyzing blood of non-human animals comprising:
a measured data acquiring device configured to measure a blood sample collected from a non-human animal and to acquire first measured data relating to a first parameter and second parameter data relating to a second parameter, the first and second measured data being obtained by measuring the blood sample;
an input device;
a display; and
a controller configured:
- to classify blood cells contained in the blood sample into a plurality of groups based upon the first and second measured data;
- to form a two-dimensional distribution chart that indicates a distribution of the blood cells contained in the blood sample based upon the first and second measured data, with the first and second parameters being set as two axes of the two-dimensional distribution chart;
- to control the display to display the two-dimensional distribution chart;
- to draw a plurality of areas on the two-dimensional distribution chart in accordance with data input by a user through the input device;
- to form a frequency distribution chart with respect to blood cells belonging to one of the areas drawn by the input device on the two-dimensional distribution chart, with one of the first and second parameters being set as an axis of the frequency distribution chart;
- to control the display to display a screen including, alongside one another, the two-dimensional distribution chart on which the areas have been drawn and the frequency distribution chart;
- to form, in response to an alteration of a shape of the one of the areas, the frequency distribution chart with respect to those blood cells belonging to the one of the areas having the altered shape; and
- to control the display to display the frequency distribution chart formed in response to the alteration of the shape of the one of the areas,
wherein the controller is further configured to receive a selection of the one of the areas in which the frequency distribution chart is formed.

11. The analyzer according to claim 10, wherein the controller is configured to receive a selection from among the first and second parameters, the selected parameter being set as an axis of the frequency distribution chart.

* * * * *